United States Patent
Pineda et al.

(10) Patent No.: US 6,779,590 B2
(45) Date of Patent: Aug. 24, 2004

(54) PHOSPHATE INVESTMENT COMPOSITIONS AND METHODS OF USE THEREOF

(75) Inventors: Rachel R. Pineda, Santa Maria, CA (US); Thomas C. Chadwick, Nipomo, CA (US)

(73) Assignee: Den-Mat Corporation, Santa Maria, CA (US)

( * ) Notice: Subject to any disclaimer, the term of this patent is extended or adjusted under 35 U.S.C. 154(b) by 0 days.

(21) Appl. No.: 10/383,653

(22) Filed: Mar. 10, 2003

(65) Prior Publication Data

US 2003/0164230 A1 Sep. 4, 2003

Related U.S. Application Data

(62) Division of application No. 09/891,275, filed on Jun. 27, 2001, now Pat. No. 6,551,396, which is a continuation of application No. 09/799,016, filed on Mar. 6, 2001, now abandoned.
(60) Provisional application No. 60/187,025, filed on Mar. 6, 2000.

(51) Int. Cl.[7] .............................. B22C 1/00; B22C 1/18
(52) U.S. Cl. ....................................... 164/518; 164/519
(58) Field of Search ............................... 164/516, 517, 164/518, 519

(56) References Cited

U.S. PATENT DOCUMENTS

| | | | |
|---|---|---|---|
| 4,604,142 A | 8/1986 | Kamohara et al. | 106/38.51 |
| 4,814,011 A | 3/1989 | Kamohara et al. | 106/38.51 |
| 5,373,891 A | 12/1994 | Kato et al. | 164/519 |

*Primary Examiner*—Kuang Y. Lin
(74) *Attorney, Agent, or Firm*—Dorsey & Whitney LLP

(57) ABSTRACT

Methods for making molding casts by a process typically referred to as "investment casting" using a novel composition is described. The composition is a phosphate bonded material that contains mono-ammonium phosphate (MAP), magnesium oxide and silica filler (quartz, cristobalite, or a mixture thereof). It has been discovered that controlling the amount and ratio of these components has a significant impact on gas permeability (porosity), set time, cast smoothness and cast softness. The most outstanding feature of the new investments is the short mold fabrication and processing time that they allow due to their high gas permeability. The investments can be placed in a burn out furnace while still wet and can be heated rapidly to the firing temperature. The casts can be broken by sandblasting the casts with glass beads. Molds made from the casts have smooth surfaces indicating that the casts are free of visible inclusions and other defects.

8 Claims, No Drawings

PHOSPHATE INVESTMENT COMPOSITIONS AND METHODS OF USE THEREOF

RELATED APPLICATIONS

This application is a divisional application of U.S. patent application Ser. No. 09/891,275, filed Jun. 27, 2001, now U.S. pat. No. 6,551,396 which is a continuation of U.S. patent application Ser. No. 09/799,016, filed Mar. 6, 2001 and abandoned Jun. 27, 2001, which claims the benefit of U.S. Provisional Application Ser. No. 60/187,025 filed Mar. 6, 2000.

TECHNICAL FIELD

The instant invention is directed to methods for making molding casts by a process typically referred to as "investment casting" or "lost wax casting." More specifically, the instant invention is directed to methods of using gas permeable phosphate bonded investment compositions that can be burned out rapidly, without fracturing, to produce strong defect-free molds.

BACKGROUND ART

"Investment casting" or "lost wax casting" is a process employed in a number of industries to make small parts out of metal, glass, porcelain and other ceramic materials. For example, the process is heavily employed in the dental industry to make dental prostheses and is utilized in the jewelry and gun industries to make small metal parts.

The first step in investment casting is to create a wax model of an object to be reproduced. This model is affixed to a wax pin called a "sprue pin" which, in turn, is positioned on a base generally made of rubber or plastic. A cylindrical ring of metal, plastic, or paper is then placed on the base so that a cylindrical cavity is created with the wax model positioned in the center of the cavity.

In the next step, investment powder, which consists of refractory fillers and a self-hardening refractory binder, is mixed with a liquid, commonly water or a silica sol, to produce a thick slurry. The investment slurry is poured into the cavity formed by the cylinder and base and over the wax model and sprue pin. The cylindrical cavity is completely filled with investment slurry so the model and sprue pin are completely covered. The investment slurry is then given time to "set" (harden) and dry. Drying can be accelerated by forced air and other techniques.

After the investment has set and dried, the base is removed and the mold (at this point consisting of the wax model, sprue pin, and overlying investment) is placed in a "burn out" furnace. The burn out furnace fires the mold at very high temperatures. The intense heat causes the wax model and sprue pin to melt and burn—hence the name "burn out." In addition the heat removes water and other volatile components. Finally, the heat chemically alters the investment material. Obviously, the type of chemical alteration that takes place will depend on the type of investment material utilized.

The mold is then removed from the furnace. The end result is a mold with a cavity that can be used to reproduce a desired object from metal, glass, porcelain, and other ceramics. To reproduce an object, a molding material (metal, glass, porcelain, ceramic) is heated until fluid and packed into the cavity. Then the mold is allowed to cool. When this has been accomplished, the mold is then broken and the casting is removed and trimmed. In the dental industry, when making prostheses, the mold material is removed by sandblasting the mold with glass beads. However, other industries use other methods—such as dropping the mold in water, creating a heat differential between the outside and inside surfaces of the mold that cracks the mold open.

There are many types of investments used in the art. Phosphate bonded investments are one type of investment material. Phosphate bonded investments are discussed extensively in Ralph W. Phillips, *Skinner's Science of Dental Materials*, 8th ed., pp. 406–410, W. B Sander's Co., Philadelphia, 1982.

One of the principle drawbacks to "investment" casting is the amount of time it takes to burn out the mold. This time is due to limitations on the rate at which the temperature can be raised during burn out.

If heat is applied too quickly, a rapid ejection of steam and other volatiles cause the walls of the mold to flake. In addition, if heating is too rapid, radial cracks will develop in the mold due to the resulting heat differential. In fact, if heating is rapid enough, the mold may actually explode.

In order to avoid the aforementioned problems, the temperature of the burn out oven is raised very slowly until the final firing temperature is reached. For molds made from conventional investment materials, the heating cycle is at least one hour. However, burn out can last as long as four hours. Moreover, the burn out furnace must be cooled between runs, further decreasing throughput.

A few attempts have been made to create investments that can be heated faster without the formation of flakes or cracks. These attempts always involve the use of additives to increase the porosity in the material. Porosity increases gas permeability, enabling steam and other volatiles to more easily escape from the material during the heating step without causing damage. However, porosity also decreases the smoothness of the mold cavity walls which may cause inclusions to form in materials molded therefrom. In addition, the inclusion of additives increases the complexity of the composition and, thereby, increases the possibility of other deleterious effects.

For example, U.S. Pat. No. 4,604,142 describes the use of starch as an additive to a gypsum-bonded investment to create, among other things "good air permeability." Similarly, U.S. Pat. No. 4,814,011 describes the use of starch as an additive to phosphate-bonded and gypsum-bonded investments that contain a wide variety of refractory fillers to provide "good air permeability." In both patents, the permeability of the investment is controlled by the use of additives and not by a judicious control of the composition of the basic investment formulation.

In addition, U.S. Pat. No. 5,373,891 describes the use of gas permeability improving additives to provide gypsum-bonded investments that can be burned out in short periods of time, thereby, producing shorter production cycle times. Once again, the permeability of the investment is controlled by the use of additives and not by control of the composition of the basic investment formulation.

SUMMARY OF THE INVENTION

The instant invention is directed to new phosphate bonded investment casting materials. The most outstanding feature of the new investments is the short mold fabrication and processing time that they allow.

For instance, some investments must be thoroughly dried before they can be burned out. In contrast, molds made from the instant investments can be placed in a furnace as soon as the investment has set. Although the molds are quite wet at this point, there are no adverse effects. This eliminates much of the processing time required by other products.

More importantly, most investments must be heated very slowly to prevent damage from volatile formation and temperature differentials. This means that the burn out oven must be cooled between each run. The slow heating ramps, and intervening cool down ramps, are very time consuming. In contrast, the new investments are sufficiently gas permeable to enable rapid heating. In fact, heating is virtually instantaneous after setting since the new investments can be placed directly into a preheated burn out furnace that is maintained at a constant elevated temperature. This completely eliminates the need for slow heating ramps and intervening cool down cycles. As a result, the burn out process is greatly accelerated. Conventional investment casting takes as long as four hours whereas casting the new investments takes less than an hour. The new investments decrease processing time at least three fold.

The new investments are well suited to the production of rush or emergency castings as well as routine production. Although the investment materials eliminate much of the time required in investment casting, they still produce smooth, defect-fee casts that are free of hairline fractures and other common deformities. The new investments produce molds that are robust enough to be used in the fabrication of dental porcelain restorations and soft enough that pressed porcelain objects may be removed from the molds without undue difficulty by sandblasting with glass beads.

The inventive phosphate bonded investments do not require the addition of modifying agents that might add undesirable properties. Instead, the invention utilizes conventional ingredients, namely, silica filler, magnesium oxide, and mono-ammonium phosphate. The discovery lies in the criticality of the amount and ratio of these ingredients. Only by using the specified components in the specified amounts can one obtain the right balance of gas permeability, set time, and other properties. Accordingly, it has been discovered that short setting times, high gas permeability, and sufficient cast softness and smoothness can only be obtained when a phosphate bonded investment comprises silica filler in the amount of 72% w/w to 80% w/wt, magnesium oxide in the amount of 7% w/w to 15% w/w and mono-ammonium phosphate in the amount of 10% w/w to 17% w/w, based on the total weight of the dry investment powder.

The particle size distribution of the silica filler is important. It should correspond to the ranges listed in the table shown below.

| US Series Screen | Screen Opening Microns | Cumulative % Retained |
| --- | --- | --- |
| 70 mesh | 212 | 0.0–0.2 |
| 100 mesh | 150 | 0.0–0.2 |
| 140 mesh | 106 | 0.1–0.8 |
| 200 mesh | 75 | 1–5 |
| 270 mesh | 53 | 10–15 |
| 325 mesh | 45 | 15–25 |

The most preferred particle size distribution for the silica filler is shown in the following table.

| US Series Screen | Screen Opening Microns | Cumulative % Retained |
| --- | --- | --- |
| 140 mesh | 106 | 0.2 |
| 200 mesh | 75 | 2 |
| 270 mesh | 53 | 12 |
| 325 mesh | 45 | 20 |

DISCLOSURE OF THE INVENTION

The investment compositions of the instant invention are phosphate bonded compositions. Phosphate bonded investments are discussed extensively in Ralph W. Phillips, *Skinner's Science of Dental Materials*, 8th ed., pp. 406–410, W. B Sander's Co., Philadelphia, 1982.

The binder in such systems is generally a mixture of mono-ammonium phosphate (MAP) and magnesium oxide. The reaction of the binder with water or aqueous silica sol can be described as follows:

$$NH_4H_2PO_4 + MgO + 5H_2O \rightarrow NH_4MgPO_4 \cdot 6H_2O$$

The ammonium magnesium phosphate salt—water complex ($NH_4MgPO_4 \cdot 6H_2O$) forms needle like crystals in a short period of time. It is this crystal formation that sets (hardens) the composition. Set compositions, however, are not synonymous with dry compositions. If one needs to dry the composition it requires significantly more time than setting. One of the benefits of the instant invention is that drying is not required.

Upon heating, the binder undergoes a number of thermal reactions. The final formulation, after burn out, is a composition comprising crystalline magnesium pyrophosphate ($Mg_2P_2O_7$) and some excess magnesium oxide (MgO).

The filler in such systems is a refractory filler. In the instant invention, the filler is silica. Silica does not undergo any chemical change during burnout. The silica employed in the instant invention contains cristobalite, quartz, or a mixture of the two. There are no particular limits on the percentages of quartz and/or cristobalite that are utilized as these concentrations will vary according to the nature of the material being cast. The particle size distribution of the silica filler is important. It should correspond to the ranges listed in the table shown below.

| US Series Screen | Screen Opening Microns | Cumulative % Retained |
| --- | --- | --- |
| 70 mesh | 212 | 0.0–0.2 |
| 100 mesh | 150 | 0.0–0.2 |
| 140 mesh | 106 | 0.1–0.8 |
| 200 mesh | 75 | 1–5 |
| 270 mesh | 53 | 10–15 |
| 325 mesh | 45 | 15–25 |

The most preferred particle size distribution for the silica filler is shown in the following table.

| US Series Screen | Screen Opening Microns | Cumulative % Retained |
| --- | --- | --- |
| 140 mesh | 106 | 0.2 |
| 200 mesh | 75 | 2 |
| 270 mesh | 53 | 12 |
| 325 mesh | 45 | 20 |

The component percentages are critical to this invention. It has unexpectedly been discovered that very small variations in component percentages have enormous affect on the investment's setting ability, gas permeability, and the quality of casts made therefrom. Only by using the specified components in the specified amounts can one obtain the right balance of gas permeability, setting time, and other properties such as cast softness and smoothness.

For the purposes of the instant invention, the amount of MAP should be from 10% w/w to 17% w/w, based on the weight of the dry investment formulation. Ideally, the amount of MAP is 14.9% by weight.

The amount of magnesium oxide should be from 7% w/w to 15% w/w, based on the weight of the dry investment formulation. Ideally, the amount of magnesium oxide is 11.0%.

The amount of silica filler makes up 72% w/w to 80% w/w of the investment. Ideally, silica filler makes up 74.1% of the investment.

In the preferred embodiment of this invention, MAP, magnesium oxide and silica filler are the only materials utilized in the investments. This is because the addition of other ingredients can have an adverse affect impact on gas permeability and/or setting time and/or cast softness and smoothness.

The investment powders described in this patent are easily made by weighing proper quantities of the ingredients and blending them as dry powders in a mixing jar. The investment powder is then packaged in 100 g foil laminate pouches that are heat sealed and stored until use. A typical investment slurry is made by mixing 100 g of the dry investment powder, and a mixture of 20 mL of 30% aqueous colloidal silica solution and 5 mL of distilled water, in a vacuum-mixing bowl. The mixture is stirred by hand with a spatula until the powder and liquid are thoroughly mixed. The mixture is then mixed under vacuum for 30–40 seconds.

The investments can be used in normal lost wax/ investment casting procedures. However, because of the unique advantages provided by the investments, the process can be significantly simplified. Thus, the invention is also directed to an improved molding process.

The improved process comprises the following steps:

(1) creating a wax model of an object to be reproduced;
(2) attaching the wax model to a "sprue pin" that, in turn, is positioned on a base; placing a hollow cylindrical ring of metal, plastic or paper on the mold base to create a cylindrical cavity;
(3) 
(4) mixing an investment powder with water, aqueous silica sol, or another suitable liquid, to create a slurry, wherein said powder comprises silica, mono-ammonium phosphate and magnesium oxide;
(5) filling the cylindrical cavity by pouring the slurry over the wax model and the sprue pin;
(6) allowing the slurry to set, thereby forming a mold intermediate that comprises the wax model, sprue pin, and overlying set investment;
(7) removing the base and placing the mold intermediate into a burn out furnace that has been preheated to at least 700° C. to make a finished mold;
(8) filling the mold with metal, glass, porcelain or other ceramic which has been heated until it is fluid; and
(9) cooling the mold and removing the finished casting.

Unlike previous formulations, molds made from the new investments can be introduced into the furnace as soon as the investment has set. Although the molds are quite wet at this point, there are no adverse effects. This eliminates some of the processing time required by previous products.

In addition, one of the benefits of the invention is that the investments set very quickly. A typical investment made in accordance with the instant invention will set within approximately 5 to 20 minutes.

The inventive investments are sufficiently gas permeable to enable rapid heating. In fact, heating can be virtually instantaneous after the investment has set or hardened. The new investments can be placed, while still quite wet, in a preheated burn out furnace that is maintained at constant high temperature. This eliminates the need for slow heat up ramps. It also eliminates the need to cool down the furnace between runs. As a result, the burn out process is greatly accelerated. In a production setting, the burn out of a 100 g mold can be completed in as little as 25 minutes at 927° C. and a 200 g mold can be burned out in 45 minutes at the same temperature.

Preferably, the mold is placed in a burn out furnace that has been preheated to at least 700° C. The molds generally remain in the furnace for at least 25 minutes and can be removed from the furnace shortly thereafter. Under normal conditions, burn out is accomplished in less than one hour.

The end result is a mold that can be used to reproduce a desired object from metal, glass, porcelain, and other ceramics. To reproduce the object, the molding material (metal, glass, porcelain, ceramic) is heated until fluid and packed into the mold. The mold is then allowed to cool. Then the mold removed by grinding, sandblasting, or other means and the casting is trimmed. In the dental industry, when making prostheses, the mold material is removed by sandblasting with glass beads. However, other industries use other methods—such as dropping the mold into water to create a heat differential between the inner and outer surfaces that cracks the mold.

The mold formed from the instant investments do not explode during burn out and do not contain hairline fractures, surface flakes or other defects. In addition, the surface finish of pressings made from molds created with the instant investments is quite smooth and free of visible inclusions and other defects. This means that the inner surfaces of the mold cavities are quite smooth which is quite surprising since most gas permeable materials generate rough surfaces. Pressing made in molds formed with the instant investments are relatively soft and the molded material can be easily removed from the cast by sandblasting or other techniques.

To better illustrate the invention, comparative and inventive examples are provided below. These examples are for the purpose of illustration and not limitation. Many other embodiments of the invention, that are not specifically set forth in the examples, are both envisioned and embraced.

COMPARATIVE EXAMPLE 1

A first investment was formulated to contain 70.0% silica fillers (58.4% quartz and 11.6% cristobalite), 14.1% MgO and 15.9% mono-ammonium phosphate. Molds made from this material had a tendency to explode when heated rapidly. In addition, the molds were hard. Therefore, it was difficult to remove porcelain pressings from the molds by sandblasting.

COMPARATIVE EXAMPLE 2

The investment formulation of comparative example 1 was reformulated by replacing some of the crystalline silica fillers with diatomaceous earth to provide gas permeability. However, these formulations were extremely hard to mix and the approach was abandoned.

INVENTIVE EXAMPLE 1

The investment formulation of comparative example 1 was then reformulated to reduce the binder content and increase the filler content in an attempt to provide greater gas permeability and make the investment softer and easier to remove. This next formulation contained 74.1% of silica filler and was quite successful. Wet molds made from it could be introduced into a burn out furnace maintained at 927° C. immediately after setting without any fear of explosion. However, according to several users, the set time was a bit too slow (13.5 min.).

INVENTIVE EXAMPLES 2–5

Then, a series of investments (examples 2–5) were formulated which all contained 74.1% silica filler (61.8% quartz and 12.3% cristobalite) and varying quantities of MgO and mono-ammonium phosphate. Example 2 contained 10.1% MgO and 15.% mono-ammonium phosphate. Example 3 contained 11.0% MgO and 14.9% mono-ammonium phosphate. Example 4 contained 12.6% MgO and 13.3% mono-ammonium phosphate. Example 5 contained 14.3% MgO and 11.6% mono-ammonium phosphate.

When these investment formulations were tried, examples 4 and 5 set rapidly. In addition, molds made from these formulations were covered with a white efflorescence after sitting at room temperature for one to three days. These for formulations were found to be quite suitable for uses where rapid set times are required and the molds formed are for immediate use.

Examples 2 and 3 exhibited slower setting properties. However, these formulations were also determined to be satisfactory for use in the rapid burnout procedure. Neither of these formulations exhibited efflorescence.

INVENTIVE EXAMPLE 6

An additional formulation (example 6), whose composition was intermediate to those of examples 3 and 4, was prepared in order to obtain a more favorable set time. The formulation was further tested in the porcelain production laboratory at Den-Mat and adapted as the preferred composition, primarily because its slightly longer set time proved to be optimal.

The following table compares the set times of the formulations described in inventive examples 1–6:

|  | Set Times |  |  |  |  |  |
|---|---|---|---|---|---|---|
|  | Example |  |  |  |  |  |
|  | 1 | 2 | 3 | 4 | 5 | 6 |
| % wt. MgO | 9.3 | 10.1 | 11.0 | 12.6 | 14.3 | 11.8 |
| % wt. MAP | 16.6 | 15.8 | 14.9 | 13.3 | 11.6 | 14.1 |
| Set Time (min.) at ~27° C. | 13.5 | 10.6 | 8.6 | 6.3 | 3.9 | — |
| Set Time (min.) at ~23° C. | — | — | 13.5 | — | — | 10.8 |

We claim:

1. A method of molding comprising the following steps:
   (i) creating a wax model of an object to be reproduced;
   (ii) attaching the wax model to a "sprue pin" that, in turn, is positioned on a base;
   (iii) placing a hollow cylindrical ring of metal, plastic, or paper on the base to form a cylindrical cavity;
   (iv) mixing an investment powder with water, aqueous silica sol, or other liquid, to create a slurry, wherein said powder comprises silica filler in an amount ranging from 72% w/w to 80% w/w mono-ammonium phosphate in an amount ranging from 10% w/w to 17% w/w and magnesium oxide in an amount ranging from 7% w/w to 15% w/w, wherein 15–25% of silica filler has a size of over 45 microns and no more than 0.2% of silica filler has a size of over 212 microns;
   (v) filling the cylindrical cavity by pouring the slurry over the wax model and the sprue pin;
   (vi) allowing the slurry to set, thereby forming a mold intermediate that comprises the wax model, sprue pin, and overlying set investment;
   (vii) removing the base and placing the mold intermediate while still wet into a burn out furnace that has been preheated to at least 700° C. to make a finished mold;
   (viii) filling the mold with metal, glass porcelain or other ceramic which has been heated until it is fluid; and
   (ix) cooling the mold and removing the finished casting.
2. The method of claim 1, wherein said slurry sets in approximately 10 to 11 minutes.
3. The method of claim 1, wherein the mold intermediate remains in the burnout furnace for at least 25 minutes and less than one hour.
4. The method of claim 1, wherein the particle size distribution of the silica filler is:

| US Series Screen | Screen Opening Microns | Cumulative % Retained |
|---|---|---|
| 70 mesh | 212 | 0.0–0.2 |
| 100 mesh | 150 | 0.0–0.2 |
| 140 mesh | 106 | 0.1–0.8 |
| 200 mesh | 75 | 1–5 |
| 270 mesh | 53 | 10–15 |
| 325 mesh | 45 | 15–25. |

5. The method of claim 1, wherein the particle size distribution of the silica filler is:

| US Series Screen | Screen Opening Microns | Cumulative % Retained |
|---|---|---|
| 140 mesh | 106 | 0.2 |
| 200 mesh | 75 | 2 |
| 270 mesh | 53 | 12 |
| 325 mesh | 45 | 20. |

6. The method of claim 1, wherein the investment powder consists essentially of 74.1% silica fillers, 11.0% magnesium oxide, and 14.9% mono-ammonium phosphate and wherein said silica contains 83.4% w/w quartz and 16.6% w/w cristobalite.
7. The method of claim 6, wherein the particle size distribution of the silica filler is:

| US Series Screen | Screen Opening Microns | Cumulative % Retained |
|---|---|---|
| 70 mesh | 212 | 0.0–0.2 |
| 100 mesh | 150 | 0.0–0.2 |
| 140 mesh | 106 | 0.1–0.8 |

-continued

| US Series Screen | Screen Opening Microns | Cumulative % Retained |
|---|---|---|
| 200 mesh | 75 | 1–5 |
| 270 mesh | 53 | 10–15 |
| 325 mesh | 45 | 15–25. |

8. The method of claim 6, wherein the particle size distribution of the silica filler is:

| US Series Screen | Screen Opening Microns | Cumulative % Retained |
|---|---|---|
| 140 mesh | 106 | 0.2 |
| 200 mesh | 75 | 2 |
| 270 mesh | 53 | 12 |
| 325 mesh | 45 | 20. |

* * * * *